United States Patent
Fiorentino et al.

(10) Patent No.: US 9,931,355 B2
(45) Date of Patent: Apr. 3, 2018

(54) COMBINATION OF COMPOUNDS DERIVED FROM GALLIC ACID FOR THE TREATMENT OF CANCER

(75) Inventors: Susana Fiorentino, Bogota (CO); John Fredy Hernandez, Bogota (CO); Claudia Uruena, Bogota (CO); Diana Castaneda, Bogota (CO); Luis Miguel Pombo, Bogota (CO); Tito Alejandro Sandoval, Valle (CO)

(73) Assignees: PONTIFICLA UNIVERSIDAD JAVERIANA, Bogota (CO); FUNDACION UNIVERSITARIA JUAN N. CORPAS, Bogota (CO)

( * ) Notice: Subject to any disclaimer, the term of this patent is extended or adjusted under 35 U.S.C. 154(b) by 0 days.

(21) Appl. No.: 14/427,552

(22) PCT Filed: Sep. 11, 2012

(86) PCT No.: PCT/IB2012/054703
§ 371 (c)(1),
(2), (4) Date: Jun. 25, 2015

(87) PCT Pub. No.: WO2014/041393
PCT Pub. Date: Mar. 20, 2014

(65) Prior Publication Data
US 2015/0313925 A1    Nov. 5, 2015

(51) Int. Cl.
| | |
|---|---|
| *A61K 31/704* | (2006.01) |
| *A61K 31/192* | (2006.01) |
| *A61K 45/06* | (2006.01) |
| *A61K 31/235* | (2006.01) |
| *A61K 31/7034* | (2006.01) |

(52) U.S. Cl.
CPC .......... *A61K 31/704* (2013.01); *A61K 31/192* (2013.01); *A61K 31/235* (2013.01); *A61K 31/7034* (2013.01); *A61K 45/06* (2013.01)

(58) Field of Classification Search
CPC ..... A61K 31/704; A61K 31/192; A61K 45/06
USPC ....................................................... 514/34
See application file for complete search history.

(56) References Cited

U.S. PATENT DOCUMENTS

| 4,968,438 A | * | 11/1990 | Soderquist | ............ | C23F 11/124 |
| | | | | | 210/750 |
| 6,063,770 A | | 5/2000 | Falcon | | |
| 6,200,568 B1 | | 3/2001 | Falcon | | |
| 7,288,273 B1 | | 10/2007 | Feldman | | |

FOREIGN PATENT DOCUMENTS

| WO | 0136436 A1 | 5/2001 |
| WO | 2005000330 A1 | 1/2005 |

OTHER PUBLICATIONS

Kashiwada et al. Antitumor Agents, 129. Tannins and Related Compounds As Selective Cytotoxic Agents. Journal of Natural Product vol. 55. No. 8. pp. 1033-1043. Aug. 1992.*
Cifuentes et al. A fraction from Petiveria alliacea induces apoptosis via a mitochondria-dependent pathway and regulates HSP70 expression. Universitas Scientiarum vol. 14 N°2-3: 125-134, 2009. www.javeriana.edu.co/universitas_scientiarum.*
Castañeda et al. A gallotannin-rich fraction from Caesalpinia spinosa (Molina) Kuntze displays cytotoxic activity and raises sensitivity to doxorubicin in a leukemia cell line. BMC Complementary and Alternative Medicine 12:38, 2012.*
N. Sakaguchi, et al; Cell death-inducing activity by gallic acid derivatives; Biological Pharmaceutical Bulletin; vol. 22; No. 5; 1999; pp. 471-475.
E. Haslam, et al; Gallotannins. The preparation and properties of some galloyl esters of quinic acid; 1963; pp. 2173-2181.

* cited by examiner

*Primary Examiner* — Yih-Horng Shiao
(74) *Attorney, Agent, or Firm* — Lucas & Mercanti, LLP

(57) ABSTRACT

The invention relates to a combination of compounds derived from gallic acid, with an antitumoral and antimetastatic activity via a mechanism that involves the induction of apoptosis and the immunogenic death of the tumor cells and the subsequent activation of the specific immune response. The invention also relates to a composition containing a combination of derivatives of gallic acid and pharmaceutically acceptable excipients for the production of useful medicaments in the treatment of cancer. The invention further relates to the use of said composition in a coadjuvant in conventional chemotherapy, reducing the doses of chemotherapeutic agents used in the treatment of cancer.

13 Claims, 10 Drawing Sheets

COMBINATION OF COMPOUNDS DERIVED FROM GALLIC ACID FOR THE TREATMENT OF CANCER

CROSS REFERENCE TO RELATED APPLICATION

This Application is a 371 of PCT/IB2012/054703 filed on Sep. 11, 2012, application which is incorporated herein by reference.

FIELD OF THE INVENTION

The present invention relates to a pharmaceutical combination and composition with antitumoral, antimetastatic and immune response-inducing activity for the treatment of cancer, which comprises one or more compounds derived from gallic acid and one or more pharmaceutically acceptable excipients for the adaptation of a pharmaceutical form.

PRIOR ART

Cancer is the main cause of death worldwide; according to the WHO statistics, 7.4 million deaths were recorded in 2004 and, in 2008, 559 000 deaths were recorded worldwide for breast cancer (WHO, 2010). Systematic therapy is the main treatment for metastatic breast cancer and includes chemotherapy, hormone therapy and monoclonal antibody-directed therapy; however, it is at the present time considered to be incurable and a mean survival time of 12 months is estimated for women who have received no treatment (Cold, S., 1993). The resistance of metastatic tumor cells to chemotherapy treatment is partly due to the development of multi-drug resistance mechanisms, which allow a rapid removal of drugs, and furthermore protects cells from death by means of the development of anti-apoptosis or survival mechanisms (Chai, To et al., 2010). Moreover, the remaining tumor cells migrate to tissues, where they can be destroyed by immune response cells, provided that the immune response has been induced during the initial phases of the carcinogenesis, or during the treatment of the tumors that have become installed (Fulton, Miller et al., 2006). Tumor treatment should then comprise the combination or mixture of molecules which induce the death of the tumor cells, in turn allowing control of the resistance mechanisms, and which also make it possible during this treatment to promote the induction of an immune response which ensures control of the metastatic cells that escape the initial direct destruction.

Only 15% of patients presenting with affected lymph nodes and who are not treated by surgery exhibit recurring cancer (Morrison, Schmidt et al., 2008), which suggests that other mechanisms, among which is the immune response, might be playing an important role in controlling metastases. The commonest sites of breast cancer metastasis are the lungs, the vertebrae, the liver, bone marrow, endocrine tissue and the central nervous system (Fulton, Miller et al., 2006), which is also reproduced in the murine model with 4T1 cells, considered highly metastatic. This pattern of metastasis increases in SCID mice, which are deficient in T or B lymphocytes, and in "nude" mice, deficient in T lymphocytes (Williams, Alosco et al., 1993) (Visonneau, Cesano et al., 1998) or even in NOG mice, deficient in NK cells and in cytokines (Dewan, Terunuma et al., 2005), which further supports the participation of the immune response in controlling metastases. In point of fact, metastasis to the sentinel lymphatic ganglions in patients with breast cancer is associated with a low potential for maturation and migration of dendritrocytes and also with a low infiltration of T CD8 lymphocytes, suggesting that immunosuppression, possibly brought about by the tumor, promotes metastatic migration (Mansfield, Heikkila et al., 2011).

The concept of multiple therapies takes it antecedence in the use of complex herbal products used in traditional medicine, which have been presented as a widely used alternative therapy (between 30% and 75% of patients with cancer worldwide) for reducing the side effects and the organic toxicity of chemotherapy, for protecting and stimulating the immune system or for preventing future neoplasms or the recurrence thereof (Richardson, 2001). Herbal products, consisting of numerous molecules, generally have an identified active component, which acts in synergy with other metabolites present in the plant combination and which, given their low concentrations, are often not identified. This synergy makes it possible to exert the biological activity with a toxicity index that is less than that of the isolated metabolites.

Among the metabolites with wide biological activity is gallic acid, which has been described as being antioxidant, antiallergic, antimutagenic, anticarcinogenic and anti-inflammatory (Gandhi and Nair, 2005). Serrano et al. in 1998 found that gallic acid and derivatives thereof (methyl, propyl, octyl and lauryl esters) induce apoptosis in various tumoral cell lines, among which are mentioned various types of leukemia, lymphoma and myeloma (Serrano, Palacios et al., 1998). In addition, substantial activity has been reported for the methyl, propyl and octyl esters of gallic acid on the HeLa tumoral cell line (Adenocarcinoma of human cervix) (Fiuza, Gomes et al., 2004). Studies directed toward determining the antitumoral activity of gallic acid and derivatives thereof (esters) have demonstrated its cytotoxic effect on the tumoral cell line L1210 (leukemia) and apoptosis induction determined by DNA fragmentation in agarose gels (Locatelli, Rosso et al., 2008).

It has been shown that tannic acid (galotannin) inhibits tumor formation, in a model with DMBA (dimethylbenzanthracene) as tumoral promoter (Mukhtar, Das et al., 1988). Moreover, it has been reported that the topical application of tannic acid inhibits, in a dose-dependent manner, ornithine decarboxylase activity, which is related with the formation of tumors in the epidermis of mice, in which the tumors were induced with TPA (12-O-tetradecanoylphorbol 13-acetate) (Gali, Perchellet et al., 1992). Similarly, it has been shown that the topical application of tannic acid inhibits carcinogenesis induced by ultraviolet light in BALB/c mice (Gensler, Gerrish et al., 1994).

Feldman K. S. in 2007 disclosed in U.S. Pat. No. 7,288,273 a method for inhibiting the release of TNF-$\alpha$ and IL-1$\beta$, which comprises the administration of a coriarin A analog (a dimeric elagitannin linked via a dihydrodigalloyl ether chain). The inventors show that the dimer analogous to coriarin A is capable of inhibiting the production of TNF-$\alpha$ and IL-1$\beta$ in peripheral mononuclear blood cells stimulated with LPS; in contrast, monomeric galotannins such as $\beta$-D-pentagalloyl glucose, induce septic shock in rat models owing to the induction of high plasmatic levels of IL-1$\beta$. These dimeric analog compounds of coriarin A and compositions thereof are proposed as TNF-$\alpha$ antagonists that are useful for treating pathologies such as septic shock associated with the overproduction of TNF-$\alpha$ and other cytokines.

U.S. Pat. Nos. 6,063,770 and 6,200,568 (Falcon J.) disclose a composition for treating cancer which comprises tannic acid or complexes thereof obtained from extracts of the species *Musa paradisiaca* and *Musa Cavendish Enano* in a proportion of between 5% and 20%. According to the invention, tannic acid precipitates the sialic (α-2,8-N-acetyl-neuraminic) acid polymers exposed at the surface of tumor cells allowing recognition of the tumor antigens by the cells of the immune system.

Patent WO 2005/000330 (Greenway F. L., et al.) reveals a method for reducing or preventing angiogenesis associated with diabetic retinopathy, macular degeneration, obesity, lupus, psoriasis, corneal neovascularization, and benign and malignant tumors, inter alia, which comprises the administration of a therapeutically effective amount of gallic acid or a derivative thereof selected from: tannic acid, methyl gallate, propyl gallate, butyl gallate, octyl gallate, ethyl gallate, lauryl gallate, ellagic acid, galloyl glucose, digalloyl glucose, trigalloyl glucose, tetragalloyl glucose, pentagalloyl glucose or glycerol trigallate. Also, it includes as anti-angiogenic agents extracts of the plants *Rubus suavissimus* S. Lee, *Diospyros kaki* L, *Rheum palmatum L, Cornus officinale Nakai, Rubus fruticosus, Rubus occidentalis* and especially the highly polar fractions of the fruit of *Punica granatum* L.

The combination of gallic acid derivatives of the present invention reduces the clonogenic capacity of tumor cells and has cytotoxic activity on various tumoral cell lines, by means of mechanisms which induce mitochondrial depolarization, and activation of caspase 3, suggesting an apoptosis induction mechanism. Furthermore, on human breast cancer tumoral cell lines (MCF7), the cell proliferation control is due mainly to stoppage of the cells in the G1 phase of the cell cycle, and the induction of an autophage mechanism, which subsequently leads to cell death. 4T1 cells reproduce in mice the pattern of metastasis of patients with breast cancer, being a good model for evaluating the activity of antimetastatic drugs, and in this model it was found that the combination of compounds of the invention reduces the size of the primary tumor, the leukemoid reaction induced by the tumor, and reduces the number of metastases in the spleen, the liver and the mesenteric lymphatic ganglions, suggesting activity on the parental tumor cells, which are the main ones responsible for metastasis. Furthermore, it induces activation of the immune response, demonstrated by the presence of T CD4 and CD8 lymphocytes specific to the tumor and producing cytokines, which proliferate when faced with the antigenic stimulus. The activity of this combination has not been evaluated previously by other authors and our results suggest that these compounds have high potential for use in cancer therapy by exerting their activity on the primary tumor and the metastases by means of: (1) a direct mechanism on the tumor cell and (2) a mechanism which involves activation of the immune response.

Aims of the Invention

In a first aspect, the invention relates to a combination of compounds derived from gallic acid, which is capable of reducing the size of the primary tumor and the number of metastases, by means of a direct mechanism on the tumor and an indirect mechanism which involves activation of the specific immune response.

In a second aspect, the invention discloses a pharmaceutical composition which comprises a combination of compounds derived from gallic acid and pharmaceutically acceptable excipients.

The use of said combination of compounds derived from gallic acid for the production of medicaments for treating cancer also forms part of the invention.

In an additional aspect, the invention includes the use of the composition of the invention as an adjuvant of conventional chemotherapy with topoisomerase inhibitors, mitosis inhibitors, alkylating agents and antimetabolites, inter alia.

In a final aspect, a method for treating cancer is disclosed, which comprises the administration of the composition of the invention simultaneously or separately with conventional chemotherapeutic agents.

DETAILED DESCRIPTION OF THE INVENTION

Figure 1:
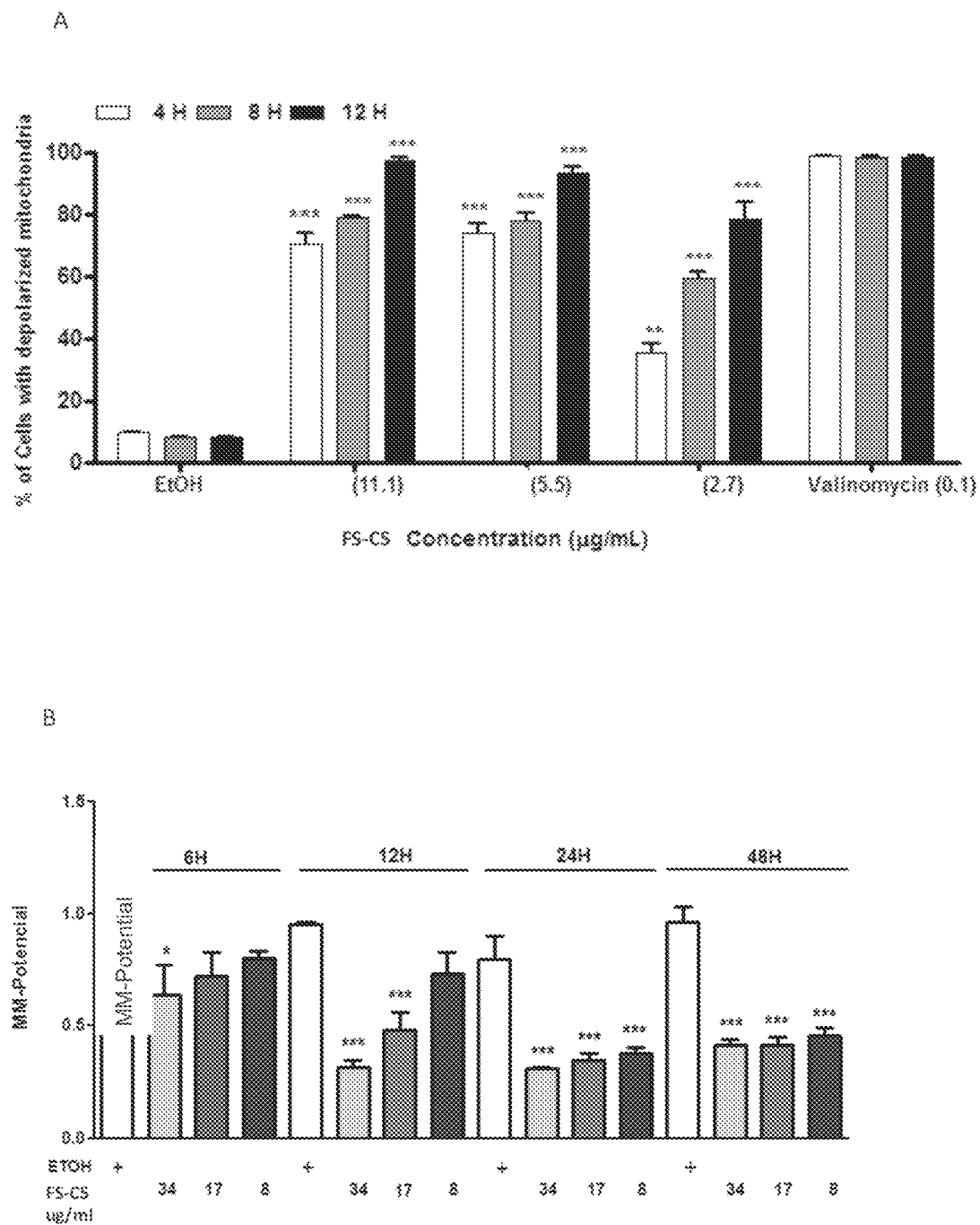
FIG. 1 shows the induction of depolarization of the mitochondrial membrane of K562 cells (A) and 4T1 cells (B) treated with the combination of the invention.

To facilitate the description of the components of the present invention, the following definitions are established for the terms used in the specification of the present invention.

The expression "compounds derived from gallic acid" refers to structures resulting from the substitutions indicated in the carbon-based structures I and II, which are compounds including at least one gallic acid molecule in their structure and which have been named generically in the present specification as gallic acid derivatives.

The expression "a combination of compounds derived from gallic acid" is understood as being the mixture of one or more compounds of formula I, of one or more compounds of formula II and of the compound 3,4,5,6-tetrakis[(3,4,5-trihydroxybenzoyl)oxy]oxan-2-yl]methyl 3,4,5-trihydroxybenzoate (common name: pentagalloyl glucose) which form the active principle or drug, which, in a suitable dosage range, is mixed with pharmaceutically acceptable excipients to generate a pharmaceutical composition.

The expression "therapeutically effective amount" is understood as meaning the dosage level of the compounds of the invention that is necessary to induce a desired biological effect in the treatment of the complaint within a risk/benefit balance that is acceptable for any medical treatment.

The expression "therapeutic" includes the treatment or prophylaxis of a complaint in a mammal, including man.

In a first aspect, the invention relates to a combination with antitumoral, antimetastatic and immune response-inducing activity for the treatment of cancer, which comprises:
   a. between 75% and 85%, relative to the total weight of the combination, of one or more compounds of formula I:

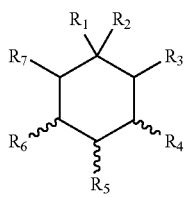

(I)

$R_1$ is hydrogen, hydroxyl, —COO⁻, —COOH
$R_2$ is selected from hydrogen, hydroxyl, —COO⁻, —COOH or

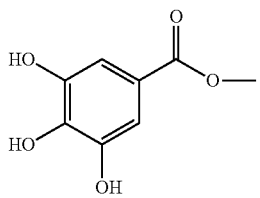

$R_3$, $R_4$, $R_5$, $R_6$ and $R_7$ are selected from hydrogen, hydroxyl or

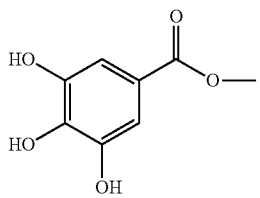

in which said compounds of formula I are preferably selected from:
3,4,5-trihydroxy-1-(3,4,5-trihydroxybenzoyl)oxycyclohexane-1-carboxylic acid,
1,4,5-trihydroxy-3-(3,4,5-trihydroxybenzoyl)oxycyclohexane-1-carboxylic acid,
1,3,5-trihydroxy-4-(3,4,5-trihydroxybenzoyl)oxycyclohexane-1-carboxylic acid,
1,3,4-trihydroxy-5-(3,4,5-trihydroxybenzoyl)oxycyclohexane-1-carboxylic acid,
1,4-dihydroxy-3,5-bis[(3,4,5-trihydroxybenzoyl)oxy]cyclohexane-1-carboxylic acid,
1,5-dihydroxy-3,4-bis[(3,4,5-trihydroxybenzoyl)oxy]cyclohexane-1-carboxylic acid,
1,3-dihydroxy-4,5-bis[(3,4,5-trihydroxybenzoyl)oxy]cyclohexane-1-carboxylic acid,
4-hydroxy-1,3,5-tris[(3,4,5-trihydroxybenzoyl)oxy]cyclohexane-1-carboxylic acid,
5-hydroxy-1,3,4-tris[(3,4,5-trihydroxybenzoyl)oxy]cyclohexane-1-carboxylic acid,
3-hydroxy-1,4,5-tris[(3,4,5-trihydroxybenzoyl)oxy]cyclohexane-1-carboxylic acid,
1-hydroxy-3,4,5-tris[(3,4,5-trihydroxybenzoyl)oxy]cyclohexane-1-carboxylic acid,
1,3,4,5-tetrakis[(3,4,5-trihydroxybenzoyl)oxy]cyclohexane-1-carboxylic acid.

Also included in the scope of the invention are the methyl, ethyl, propyl, butyl, pentyl, hexyl and heptyl esters and the addition salts with mineral acids or bases with alkali metals and alkaline-earth metals, such as: calcium, lithium, magnesium, aluminum, sodium, potassium, of the compounds mentioned previously.
   b. between 10% and 20%, relative to the total weight of the combination, of one or more compounds of formula II:

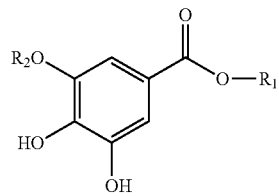

(II)

in which:
$R_1$ is selected from hydrogen, methyl, ethyl, propyl, butyl, pentyl, hexyl or heptyl
$R_2$ is selected from hydrogen or

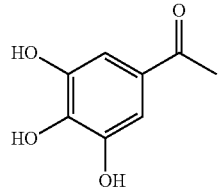

with the condition that $R_1$ and $R_2$ are not simultaneously hydrogen in which said compounds of formula II are preferably selected from:
3,4,5-trihydroxybenzoate
methyl 3,4,5-trihydroxybenzoate
ethyl 3,4,5-trihydroxybenzoate
propyl 3,4,5-trihydroxybenzoate
butyl 3,4,5-trihydroxybenzoate
pentyl 3,4,5-trihydroxybenzoate
hexyl 3,4,5-trihydroxybenzoate
heptyl 3,4,5-trihydroxybenzoate
3,4-dihydroxy-5-(3,4,5-trihydroxybenzoyl)oxybenzoate
methyl 3,4-dihydroxy-5-(3,4,5-trihydroxybenzoyl)oxybenzoate
ethyl 3,4-dihydroxy-5-(3,4,5-trihydroxybenzoyl)oxybenzoate
propyl 3,4-dihydroxy-5-(3,4,5-trihydroxybenzoyl)oxybenzoate butyl 3,4-dihydroxy-5-(3,4,5-trihydroxybenzoyl)oxybenzoate pentyl 3,4-dihydroxy-5-(3,4,5-trihydroxybenzoyl)oxybenzoate hexyl 3,4-dihydroxy-5-(3,4,5-trihydroxybenzoyl)oxybenzoate heptyl 3,4-dihydroxy-5-(3,4,5-trihydroxybenzoyl)oxybenzoate c. between 0.1% and 8%, relative to the total weight of the combination, of the compound 3,4,5,6-tetrakis[(3,4,5-trihydroxybenzoyl)oxy]oxan-2-yl]methyl 3,4,5-trihydroxybenzoate (common name: pentagalloyl glucose).

Said combination may be used for the preparation of medicaments with antitumoral, antimetastatic and immune response-inducing therapeutic activity that are useful in the treatment of cancer.

In a second aspect, the invention relates to a pharmaceutical composition with antitumoral, antimetastatic and immune response-inducing activity for the treatment of cancer, which comprises:

(a) one or more compounds of formula I:

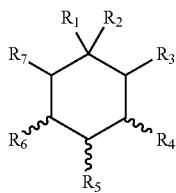
(I)

$R_1$ is hydrogen, hydroxyl, —COO$^-$, —COOH $R_2$ is selected from hydrogen, hydroxyl, —COO$^-$, —COOH or

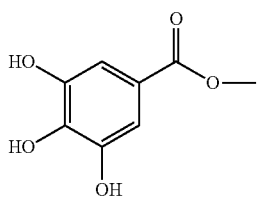

$R_3$, $R_4$, $R_5$, $R_6$ and $R_7$ are selected from hydrogen, hydroxyl or

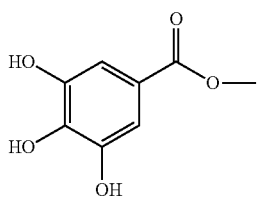

(b) one or more compounds of formula II:

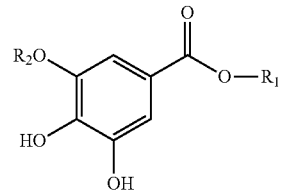
(II)

in which:

$R_1$ is selected from hydrogen, methyl, ethyl, propyl, butyl, pentyl, hexyl or heptyl $R_2$ is selected from hydrogen or

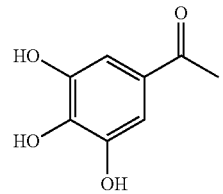

with the condition that $R_1$ and $R_2$ are not simultaneously hydrogen, (c) the compound 3,4,5,6-tetrakis[(3,4,5-trihydroxybenzoyl)oxy]oxan-2-yl]methyl 3,4,5-trihydroxybenzoate, (d) and one or more pharmaceutically acceptable excipients for the adaptation of a liquid, solid or heterodispersed pharmaceutical form.

Said composition may be formulated with one or more pharmaceutically acceptable excipients for oral administration in solid or liquid pharmaceutical forms, for topical administration in heterodispersed forms (W/O creams, O/W creams, gels and ointments, inter alia) and for parenteral or rectal administration. The compositions of the invention may be administered to humans and other mammals via the oral, rectal, parenteral, topical, intravaginal or buccal route or as a nasal or oral spray.

The compositions for oral administration which contain the combination of compounds of the invention include the conventionally used oral pharmaceutical forms, such as: tablets, capsules, buccal forms and oral liquids, suspensions or solutions. The capsules may contain mixtures of the active agents with inert excipients and/or diluents such as: pharmaceutically acceptable starches (for example corn, potato or starch), sugars, artificial sweeteners, powdered celluloses (carboxymethylcellulose, methyl cellulose, ethyl cellulose, hydroxypropyl methyl cellulose), flours, gelatins and gums, inter alia.

The compositions in tablet form may be produced via conventional compression, wet granulation or dry granulation methods and use may be made of excipients such as: diluents, lubricants, disintegrants, surfactants, suspension agents or stabilizers, including but not limited to magnesium stearate, stearic acid, talc, sodium lauryl sulfate, microcrystalline cellulose, carboxymethylcellulose, polyvinylpyrrolidone, gelatin, alginic acid, acacia gum, xanthan gum, sodium citrate, complex silicates, calcium carbonate, lactose, kaolin, mannitol, sodium chloride, dry starches and sucrose in pharmaceutically acceptable grades. Similarly, the oral compositions revealed in the invention may be conventional formulations or sustained-release or controlled-release formulations which alter the absorption of the active agents.

The formulations for parenteral administration of the invention may contain pharmaceutically acceptable excipients, including, but not limited to: surfactants (lecithin, acacia, tragacant, polyoxyethylated fatty acid esters of sorbitan, polyoxyethylated fats, polyoxyethylated oleotriglycerides, polyoxyalkylene derivatives of propylene glycol, condensation products of polyethylene oxide and fatty alcohols, alkanolphenols or fatty acids), tonicity modifiers (sodium chloride, sucrose, dextrose, mannitol, lactose, trehalose, glucose, glycine), solvents (water, propylene glycol, polyethylene glycol, glycerol, ethanol), pH regulators (phosphate buffer, citrate, lactate, glycine, Tris, sodium bicarbonate), antioxidants (α-tocopherol, BHT, BHA), chelating agents (EDTA) and viscosity modifiers (carboxymethylcellulose, croscarmellose, hydroxypropylcellulose).

The dosage levels of the combination of compounds of the invention in the pharmaceutical composition provided by the invention may vary in order to reach the desired therapeutic response depending on the physiological and pathological conditions of the individual, the formulation and the route of administration. The selected dosage levels depend specifically on the therapeutic power of the compounds, the route of administration, the severity of the condition treated and the prior medical history of the patient to be treated.

The total daily dose of the combination of the invention used in the composition of the invention may vary within the range from 0.001 to 1000 mg/kg/day. For oral administration purposes, the preferred doses are within the range from 0.001 to 5 mg/kg/day and parenterally within the range from 0.0001 to 2 mg/kg/day. If required, the effective daily dose may be divided into multiple doses for administration purposes, and consequently the invention comprises compositions of single doses which contain the effective amount or multiple doses which reach the effective daily dose after several administrations.

The pharmaceutical composition of the invention comprises as active principle compounds of formula I, II and pentagalloyl glucose in a range of between 0.01% and 90% by weight of the composition, with the condition that between 75% and 85% of said active principle corresponds to one or more compounds of formula I.

In another aspect, the invention relates to the use of the composition of the invention for the preparation of medicaments with antitumoral, antimetastatic and immune response-inducing therapeutic activity which are useful in the treatment of cancer.

Similarly, the invention includes the use of the composition of the invention as adjuvant of conventional chemotherapy with topoisomerase inhibitors, mitosis inhibitors, alkylating agents and antimetabolites, inter alia, for the treatment of cancer. Said adjuvant activity is reflected in the decrease of the required dose of chemotherapeutic agent, consequently reducing the systematic toxicity of the therapy.

A method for treating cancer which comprises the concomitant or separate administration of the composition of the invention with conventional chemotherapeutic agents of the type such as topoisomerase inhibitors, mitosis inhibitors, alkylating agents and antimetabolites in doses lower than those required in conventional chemotherapy is included within the scope of the invention.

PREFERRED EMBODIMENTS OF THE INVENTION

One of the combinations of compounds derived from gallic acid evaluated in the course of the examples presented in the specification of the invention has been generically named FA-CS. This combination comprises between 75% and 85% in weight/weight percentage of compounds of formula I, between 10% and 20% in weight/weight percentage of compounds of formula II, and between 0.1% and 8% relative to the total weight of the combination of the compound pentagalloyl glucose (3,4,5,6-tetrakis[(3,4,5-trihydroxybenzoyl)oxy]oxan-2-yl]methyl 3,4,5-trihydroxybenzoate), in accordance with the following table:

|  | w/w % relative to the total of the combination |
|---|---|
| Compounds of formula I (75-85 w/w % relative to the total of the combination) | |
| 3,4,5-trihydroxy-1-(3,4,5-trihydroxybenzoyl)oxycyclohexane-1-carboxylic acid (1-O-galloylquinic acid), 1,4,5-trihydroxy-3-(3,4,5-trihydroxybenzoyl)oxycyclohexane-1-carboxylic acid (3-O-galloylquinic acid), 1,3,5-trihydroxy-4-(3,4,5-trihydroxybenzoyl)oxycyclohexane-1-carboxylic acid (4-O-galloylquinic acid), 1,3,4-(trihydroxy-5-(3,4,5-trihydroxybnezoyl)oxycyclohexane-1-carboxylic acid (5-O-galloylquinic acid), | 55-70 |
| 1,4-dihydroxy-3,5-bis[(3,4,5-trihydroxybenzoyl)oxy]cyclohexane-1-carboxylic acid (3,5-O-digalloylquinic acid), 1,5-dihydroxy-3,4-bis[(3,4,5-trihydroxybenzoyl)oxy]cyclohexane-1-carboxylic acid (3,4-O-digalloylquinic acid), 1,3-dihydroxy-4,5-bis[(3,4,5-trihydroxybenzoyl)oxy]cyclohexane-1-carboxylic acid (4,5-O-digalloylquinic acid), | 10-20 |
| 4-hydroxy-1,3,5-tris[(3,4,5-trihydroxybenzoyl)oxy]cyclohexane-1-carboxylic acid (1,3,5-tri-O-galloylquinic acid), 5-hydroxy-1,3,4-tris[(3,4,5-trihydroxybenzoyl)oxy]cyclohexane-1-carboxylic acid (1,3,4-tri-O-galloylquinic acid), 3-hydroxy-1,4,5-tris[(3,4,5-trihydroxybenzoyl)oxy]cyclohexane-1-carboxylic acid (1,4,5-tri-O-galloylquinic acid), 1-hydroxy-3,4,5-tris[(3,4,5-trihydroxybenzoyl)oxy]cyclohexane-1-carboxylic acid (3,4,5-tri-O-galloylquinic acid). | 1-10 |
| Compounds of formula II (10-20 w/w % relative to the total of the combination) | |
| 3,4-dihydroxy-5-(3,4,5-trihydroxybenzoyl)oxybenzoate | 1-10 |

-continued

|  | w/w % relative to the total of the combination |
|---|---|
| methyl 3,4-dihydroxy-5-(3,4,5-trihydroxybenzoyl)oxybenzoate | 1-10 |
| methyl 3,4,5-trihydroxybenzoate | 0.1-5 |
| 3,4,5,6-tetrakis[(3,4,5-trihydroxybenzoyl)oxy]oxan-2-yl]methyl 3,4,5-trihydroxybenzoate (pentagalloyl glucose) | 0.1-8 |

The scientific facts upon which the present invention is based, which should not be understood as limiting the invention, are presented hereinbelow for illustrative purposes.

Cell Lines

The human cell lines used were K562 (human erythroleukemia) MCF7 (human breast cancer) and A375 (human melanoma). The murine cell lines used were Mel Rel (murine melanoma) and 4T1 (murine mammary cancer). These cells were maintained in RPMI 1640 medium supplemented with 10% fetal calf serum, 2 mM of L-glutamine, 100 U of penicillin, 100 µg/ml of streptomycin and 0.01 M of HEPES (Eurobio, Toulouse, FR) at 37° C. with 5% $CO_2$ under a humid atmosphere. The cell line 4T1 was also maintained with 1 mM of sodium pyruvate (Eurobio, Toulouse, FR). For the assays on normal cells, human mononucleocytes from the venous peripheral blood of healthy donors (PBMC) were obtained, and were separated by centrifugation using a Ficoll-Hypaque density gradient (GE Healthcare Bio-Sciences AB, Bjorkgatan, Uppsala, Sweden).

Example 1. Cytotoxic Activity of the FA-CS Combination on Various Tumoral Cell Lines The cytotoxic effect of the combination of the invention on tumor cells and normal cells was evaluated by direct microscopic observation and via assays with MTT (Sigma, Saint Louis Mo., USA). To do this, the tumor cells in suspension ($5 \times 10^3$ cells/well) or adherent ($3 \times 10^3$ cells/well) were placed in 96-well plates with various concentrations of FA-CS: 125, 62.5, 31.2, 15.6, 7.8, 3.9, 1.95 and 0.975 µg/mL for 48 hours (h). To evaluate the effect of the FA-CS combination on normal cells, PBMCs ($2 \times 10^5$ cells/well) were obtained and were first stimulated for 12 hours with phytohemagglutinin (PHA) (Invitrogen Corp, Grandlsland, N.Y., USA) and cultured in 96-well plates with the same concentrations of the combination. Ethanol (EtOH) at 0.02% was used as negative control and, as positive control, use was made of various antitumoral drugs such as doxorubicin, camptothecin, vincristine and taxol, for which the 50% inhibitory concentration (1050) was determined to be taken as base for the subsequent assays. After incubation, the culture medium was removed and 50 µl of RPMI 1640 medium free of phenol red (Eurobio, Toulouse, FR) were added. 50 µl of MTT (1 mg/ml) [3-(4,5-dimethylthiazol-2-yl)-2,5-diphenyltetrazolium bromide] (Sigma, Saint Louis Mo., USA) were added to each well and incubated for 4 hours at 37° C. The formazan crystals were dissolved with dimethyl sulfoxide (DMSO) and the optical density was measured at 540 nm in a Multiskan MCC/340 machine (Labsystems, Thermo Fisher Scientific, Waltham, USA).

The cytotoxic effect of FA-CS was evaluated with MTT on various tumoral cell lines. The 1050 value on the various cell lines was calculated using the Minitab software. Table 1 shows the various concentrations corresponding to the 1050 calculated for each cell line. These results show that the human breast cancer line MCF-7 presents the highest sensitivity, with an 1050 of 4.04 µg/ml, followed by the human erythroleukemia line K562 (27.1 µg/mL) and human melanoma A375 (43.4 µg/mL). For the murine cell lines 4T1, the concentrations obtained are higher, with values of 34.1. The line Mel Rel, not shown in the table, has an 1050 of 14.1 µg/mL. The IC50 of the conventional drugs is also shown in table 1.

TABLE 1

50% inhibitory concentration (µg/mL) of the FA-CS combination of the invention and of conventional drugs on tumoral cell lines and normal mononuclear cells

| Linea celular/ Tratamiento | FA-CS (µg/mL) | Ácid o Galico (µg/mL) | Doxorrubicin a (µg/mL) |
|---|---|---|---|
| 4T1 | 34.1 ± 1.6 | 96.2 ± 0.0 | 0.5 ± 0.1 |
| MCF7 | 62.1 ± 1.9 | 4.07 ± 0.04 | 5.3 ± 0.5 |
| A375 | 43.3 ± 1.9 | ND | 0.02 ± 0.1 |
| K562 | 44.5 ± 4.0 | 18.2 ± 0.1 | 0.2 ± 0.1 |
| PBMC + PHA | >125 ± 1.0 | ND | 2023 ± 0.2 |
| Fibroblastos | 12.0 ± 0.04 | NP | 0.4 ± 0.1 |

Key: Cell line/treatment
FA-CS
Gallic acid
Doxorubicin
Fibroblasts

The evaluation of the cytotoxic activity of FA-CS on the normal mononuclear cells was higher than the highest dose of FA-CS, and on fibroblasts, the IC50 was also higher than that of the control used: doxorubicin.

Example 2. Induction of Apoptosis in Tumor Cells by the FA-CS Combination of the Invention As an indicator of early apoptosis, the changes in potential of the mitochondrial membrane of K562 and 4T1 cells were evaluated at intervals of 4, 8, 12, 24 and 48 hours by flow cytometry using the lipophilic cationic probe JC-1 (5,5",6,6"-tetrachloro-1,1",3,3"-tetraethylbenzimidolcarbocyanine iodide) (Sigma, Saint Louis Mo., USA). JC-1 (10 µg/mL in PBS) was added to $3 \times 10^5$ cells/mL and incubated for 10 minutes at 37° C. The fluorescence intensity of the JC-1 was quantified in an FACSCalibur flow cytometer (Becton Dickinson, New Jersey, USA) or an FACSDiva flow cytometer (Becton Dickinson, New Jersey, USA) and the data analysis was performed using the CellQuest Pro software (Becton Dickinson, New Jersey, USA) or the Flowjo software (Tree Star Inc., Ashland, USA). All the treatments were performed in triplicate and the results were expressed as the mean±SEM. The apoptosis was determined by measuring the exposure of phosphatidylserine via labeling with annexin V/propidium iodide (Molecular Probes). To do this, $5 \times 10^5$ 4T1 cells were treated with the FA-CS combination or EtOH (negative control) for 24 and 48 hours. After the treatment, the cells were collected, centrifuged and resuspended in annexin buffer (HEPES 100 mM, NaCl 140 mM, CaCl$_2$ 2.5 mM) and annexin V for 8 minutes. Next, 2.5 µl of propidium iodide were added over 2 minutes. After incubation, the readings were taken immediately using an FACSAria flow cytometer (Becton Dickinson).

Figure 2:
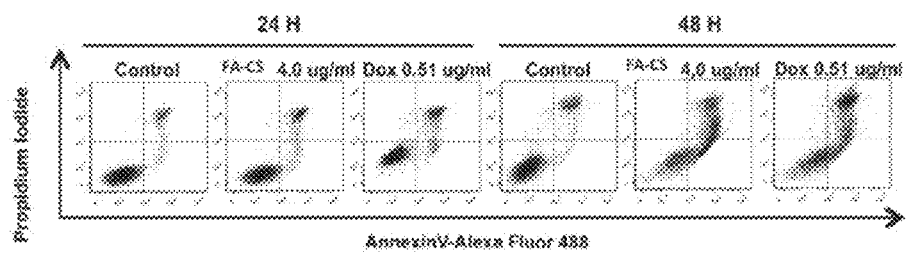
FIG. 2 shows the induction of apoptosis on tumoral cell lines by treatment with the combination of the invention.
Figure 2:
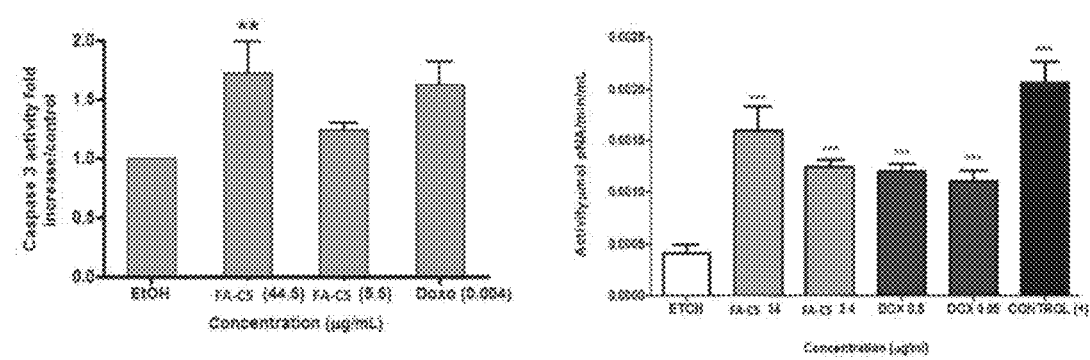
Figure 2:
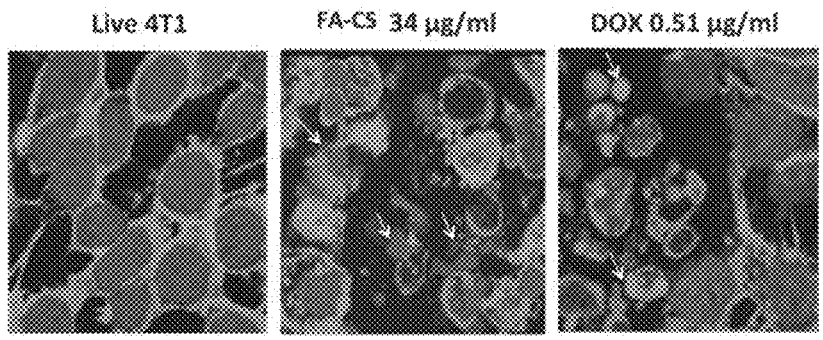

As may be seen in FIG. 2A, the FA-CS combination induces an increase in the percentage of cells whose mitochondrial membrane is depolarized. This effect is time-dependent and is equivalent for the two cell lines evaluated.

In addition, the activation of caspase 3 and the DNA fragmentation induced by FA-CS were determined. To evaluate the caspase 3 activity, the Caspase-3 Colorimetric Assay Kit was used (R&D Systems Inc., Minneapolis, Minn., USA) according to the manufacturer's instructions. Briefly, 2×10$^6$ cells (K562 or 4T1) were cultured in the presence or absence of the FA-CS combination for 48 hours. EtOH at 0.02% was used as negative control and doxorubicin was used as positive control. After incubation, the cells were centrifuged at 250×g for 10 minutes and the resulting pellet was lysed for 10 minutes in ice and centrifuged at 10 000×g for 1 minute. The enzymatic reaction was performed in 96-well plates, using 50 µl of cell lyzate (100-200 µg of total protein) and 50 µl of the reaction buffer supplemented with 10 µl of fresh DTT and 5 µl of the caspase 3 colorimetric substrate (DEVD-pNA). After 1 to 2 hours of incubation at 37° C., the protease activity of caspase 3 was measured in a spectrophotometer to 405 nm (Labsystems, Thermo Fisher Scientific, Waltham, USA). The amount of caspase 3 activity in the cell lyzate is directly proportional to the color obtained in the reaction. The results are presented as a relative increase in caspase 3 activation induced by FA-CS or the conventional drug relative to the control. FIG. 2B shows that the combination of the invention induces caspase 3 activity in the treated cells: K562 on the left and 4T1 on the right.

As a final step in the induction of death by apoptosis, we evaluated the DNA fragmentation by staining with DAPI via fluorescence microscopy. K562 cells (2×10$^5$ cells) and 4T1 (2×10$^5$ cells) were cultured for 24 hours on glass slides (13 mm in diameter) pretreated with type II collagen (Sigma, Saint Louis Mo., USA). Once adhered, the cells were treated with FA-CS or with its respective controls. Doxorubicin was used as positive control, and EtOH 0.02% was used as negative control, for 48 hours at 37° C. and 5% CO$_2$. After treatment, the cells were washed with pH 7.2 PBS and fixed with paraformaldehyde (PAF) (Sigma, Saint Louis Mo., USA) at 2% for 30 minutes at 4° C. The fixed cells were washed twice with 2% PBS-BSA, incubated with cold acetone for 1 minute, washed with 2% PBS-BSA and stained with 300 nM of DAPI (Sigma, Saint Louis Mo., USA) for 5 minutes. Finally, the cells were treated with antifade kit (Molecular Probes, InvitrogenCorp, Carlsbad, Calif., USA) and analyzed by fluorescence microscopy using a FluoView 1000 confocal microscope from Olympus (CenterValley Pa., USA). FIG. 2C clearly shows the nuclei fragmented in response to the treatment with the combination of the invention in comparison with ethanol in 4T1 cells.

By collating the results presented, it is found that the FA-CS combination induces apoptosis of the tumor cells via the mitochondrial route. Analysis of the kinetics of expression of phosphatidylserine, which constitutes a marker of death by apoptosis, showed that the tumor cells express phosphatidylserine, recognized by marking with annexin V, and that the death is not an event which does not induce early but rather late necrosis, as observed in FIG. 2A.

Example 3. Reduction of the Clonogenic Capacity of Tumor Cells by Treatment with the Combination of the Invention To evaluate the effect of the FA-CS combination in the long term on the clonogenic capacity of tumor cells, the lines K562 and 4T1 (1.0×10$^5$ cells/well) were treated with FA-CS or with a respective control thereof for 6 hours. Vincristine and doxorubicin were used as positive control and 0.02% EtOH was used as negative control. After the treatment, 20 000 cells were plated out in 60 mm Petri dishes with 0.5-0.3% agar for 14 days at 37° C. with 5% CO$_2$ and subsequently stained with 0.4% crystal violet. The colonies containing more than 50 cells were counted. All the treatments were performed in triplicate and the results are expressed as the mean±SEM of the total number of colonies.

Figure 3:
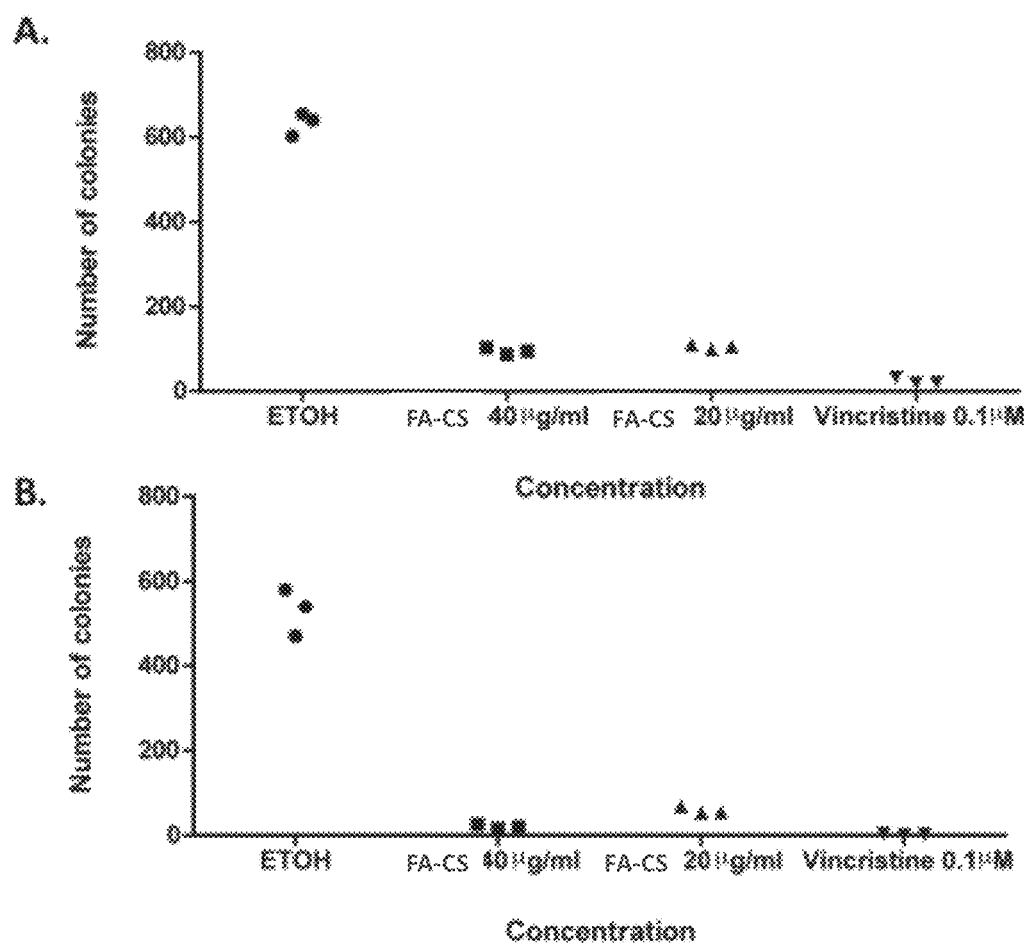
FIG. 3 shows the reduction in the colony-forming capacity of 4T1 and K562 cells treated with a combination of the invention.

As seen in FIG. 3, after 14 days in culture, the capacity for proliferation of the tumor cells K562 (3A) and 4T1 (3B) was reduced in comparison with the negative control (EtOH). Similar results were observed for the respective positive controls.

Example 4. Coadjuvant Activity of the FA-CS Combination with Conventional Chemotherapeutic Agents The coadjuvant activity of the FA-CS combination of the invention was determined on the MCF-7 line at a concentration of 1.6 µg/mL (27 times less than the IC50) in co-treatment with chemotherapeutic agents such as: doxorubicin, vincristine, taxol and camptothecin at sub-optimal concentrations. To evaluate the cell viability, the MTT test was used. MCF-7 cells (3×10$^3$ cells/well) were cultured in 96-well plates and treated for 6 hours with the FA-CS combination, washed and incubated in fresh medium with each of the chemotherapeutic drugs for 48 hours at 37° C. in a humid atmosphere with 5% CO$_2$. The MTT assay was performed as described previously. The results are expressed as a percentage of cell viability relative to the control.

Figure 4:
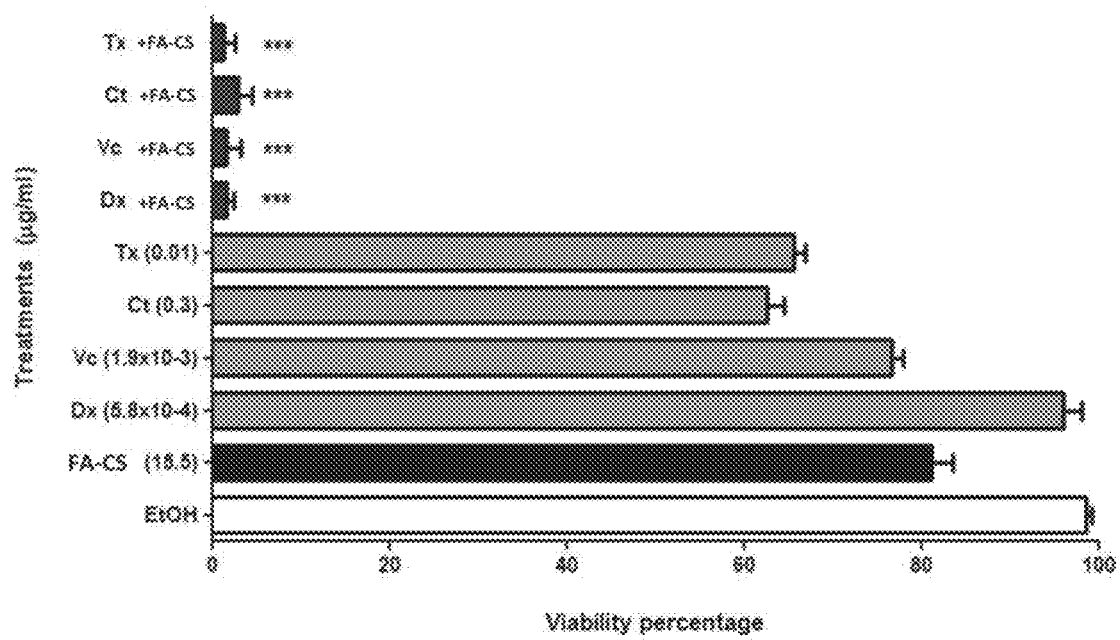
FIG. 4 shows the adjuvant activity of the combination of the invention (treatment with sub-optimal doses of the combination and of chemotherapeutic agents) on human breast cancer tumoral cells.

FIG. 4 shows that the combination of doxorubicin, vincristine and camptothecin with the FA-GS combination of the invention significantly reduces the cell viability. These results show that treatment with the combination of the invention can sensitize tumor cells to treatment with conventional drugs, reducing the doses required in the treatments and consequently the systematic toxicity associated with the chemotherapy.

Example 5. Inhibition of In Vivo Growth of the Primary Tumor of 4T1 Tumor Cells Induced by the Combination of the Invention and Reduction of Metastases to Different Organs Female BALB/c mice 6 to 12 weeks old were acquired from Charles River Laboratories (Wilmington, Mass.) and kept in our animal investigation center. The mice were kept in polyethylene cages and fed ad libitum with food and water in a room with controlled temperature and relative humidity and with 12-hour cycles of lighting-darkness. The mice were acclimatized for 1 week prior to use.

4T1 cells (1×10$^4$) were resuspended in phosphate-buffered saline and injected into the right-side mammary gland (subcutaneously, s.c., day 0). 5 days after the inoculation, the mice were treated intraperitoneally with the combination (9.3 or 18.7 mg/kg) or the control, twice a week. To evaluate the effect of the combination, groups of 7-8 mice were separated for differential treatment. Blood samples were taken weekly via the caudal vein to determine the number of leukocytes, using a hemocytometer (ABX Micros 60®). The tumor volume was determined twice a week using vernier calipers, and was calculated using the following formula: tumor volume $(mm^3)=[(width)^2 \times length]/2$. The mice were sacrificed when the primary tumor reached 2000 $mm^3$; after death, the primary tumor was weighed.

Figure 5:
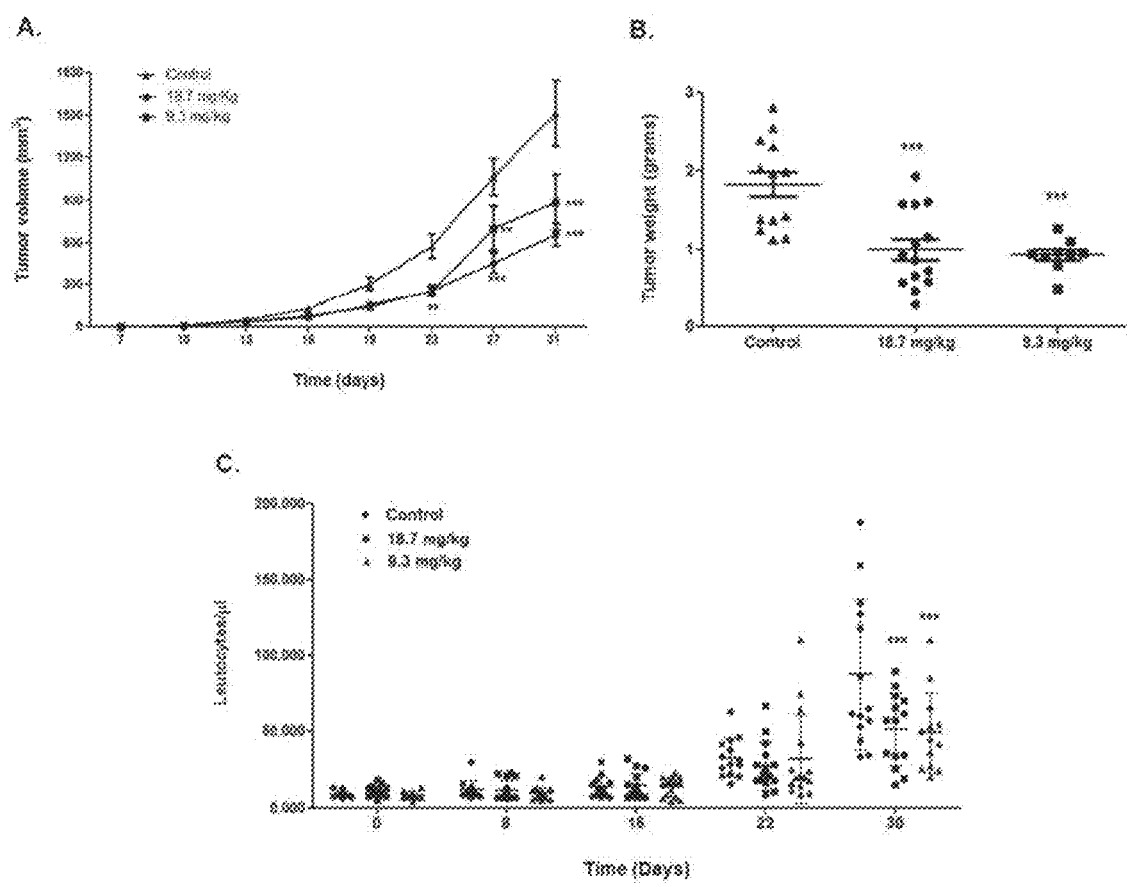
FIG. 5 shows the effect of the combination of compounds derived from gallic acid of the invention on the diameter and weight of the tumor in an in vivo model of murine breast cancer.
Figure 6:
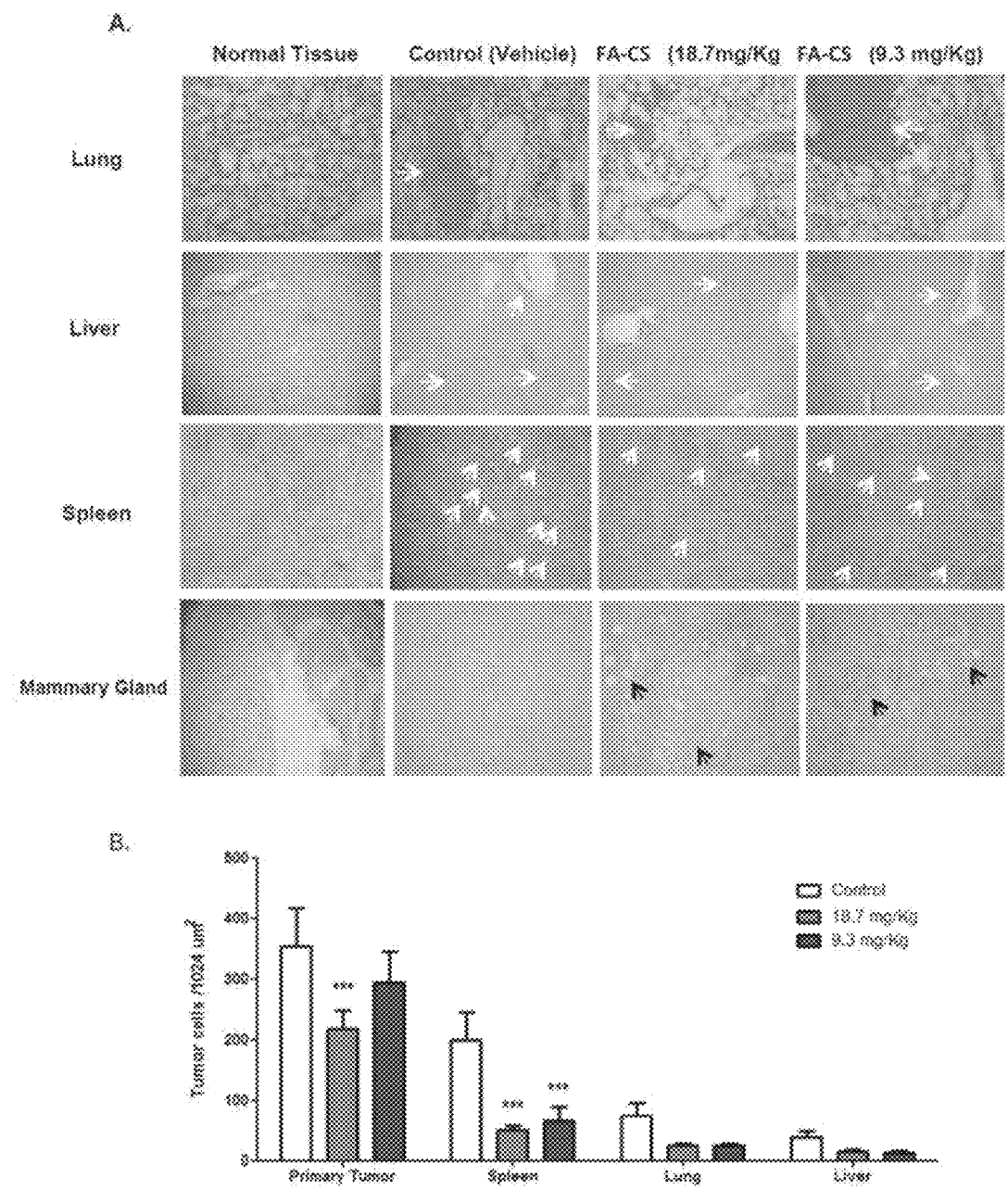
FIG. 6 shows the reduction of metastatic foci and of megakaryocytes in parenchymatosus organs of animals treated with a combination of compounds derived from gallic acid of the invention.

The dose of the combination was established after determining the in vivo toxicity for the purpose of establishing the minimum lethal dose that can be used in therapy. As is seen in FIGS. 5A and B, FA-CS significantly reduces the diameter of the tumor when compared with the negative control from 22 up to 30 days of treatment. When the mice were sacrificed, at the end of the treatment, the weight of the tumor was calculated, and a reduction in the weight of the tumor may clearly be seen with the treatment at the two concentrations used versus the negative control. Similarly, FIG. 5C shows that the treatment reduces the leukemoid reaction which occurs in this model as a consequence of the growth of the tumor. On performing the histopathological analyses of the various organs such as the lungs, liver, bone marrow, brain and spleen, a reduction in the number of tumor cells was observed in the organs of the mice treated with the FA-CS combination versus the negative control (FIG. 6A).

After treatment with the FA-CS combination, the primary tumor, the lungs, spleen, liver, brain and bone marrow were collected and sectioned. Next, the tissues were fixed in 10% formaldehyde (Sigma-Aldrich), embedded in paraffin and sliced into 2 μm sections for staining with hematoxylin-eosin (H&E). The metastatic tumor cells infiltrating the various organs were evaluated in each tissue and were counted using a micrometric grid (resolution power 10× and 40×) on an optical microscope. FIG. 6B shows the decrease in the number of metastases in the spleen and the lung, and also the decrease in the number of tumor cells present in the primary tumor in the mice treated with the combination versus the controls.

Figure 7:
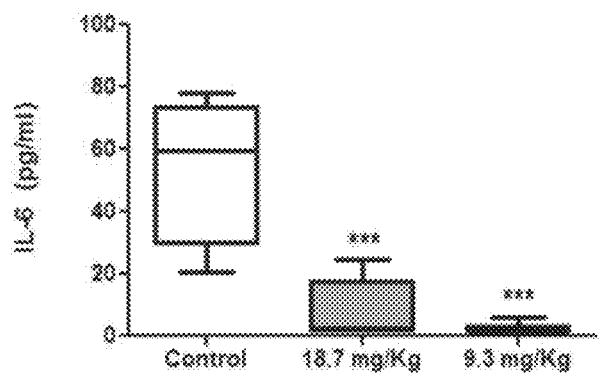
FIG. 7 shows the reduction in interleukin 6 production in mice with a tumor treated with the combination of compounds derived from gallic acid.

The serum of the mice treated with the combination was collected by cardiac puncture and the measurement of the serum cytokines was performed using the mouse inflammation CBA kit (Becton Dickinson). The experiments were performed in duplicate. The results are expressed as the mean of two independent experiments. FIG. 7 shows a decrease in seric IL6 in response to the treatment with various doses of the FA-CS combination. These results suggest that treatment with the FA-CS combination has an effect on the host's inflammatory response, which correlates with a decrease in the tumor diameter and better control of the metastases, confirming the antitumoral role of the FA-CS combination of the invention.

Example 6. Treatment with the FA-CS Combination Promotes Immunogenic Death in 4T1 Cells The effect of FA-CS on the release of various hazard signals that were involved in the generation of immunogenic cell death was evaluated on 4T1 cells. For the evaluation in the expression of calreticulin (CRT), 4T1 cells were cultured in 12-well plates and treated with the negative control (ethanol), the FA-CS combination (34 μg/ml) and doxorubicin (0.51 μg/ml) for 24 hours. The cells were labeled with the primary antibody (anti-CRT, ab2907, abcam) diluted in cold blocking buffer (2% FCS in PBS) for 30 minutes, washed and incubated with the secondary antibody conjugated to Alexa Fluor 488 (Molecular Probes) in blocking buffer for 30 minutes. The cells were taken up in an FACSAria II flow cytometer (Becton Dickinson) to identify the CRT in the plasma membrane. The fluorescence intensity of the stained cells was evaluated on a negative water population. The analyses were formed using the FlowJo software (Tree Star Inc).

For detection of the HMGB1 protein, 4T1 cells ($1 \times 10^4$) were cultured on glass slides in 12-well plates and treated with the negative control (ethanol), the FA-CS combination (34 μg/ml) and doxorubicin (0.51 μg/ml) for 24 hours. For the intracellular staining of HMGB1, the cells were labeled with the primary antibody (anti-HMGB1, ab18256, Abcam) for 60 minutes, washed 3 times with PBS and incubated for 30 minutes with the secondary antibody conjugated to Alexa Fluor 488 (Molecular Probes). After this incubation, the cells were labeled with DAPI (Molecular Probes) for 5 minutes and the fluorescence was preserved with the Prolong Antifade Kit (Molecular Probes) and analyzed with a confocal fluorescence microscope (FluoView 1000).

Figure 8:
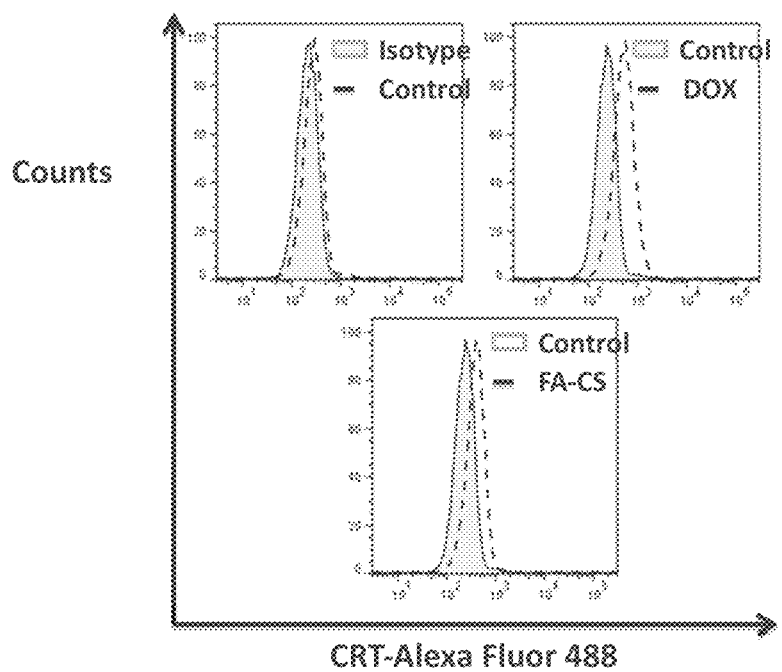
FIG. 8 shows the membrane expression of calreticulin and the mobilization of HMGB1 from the nucleus to the cytoplasm, in tumor cells treated with the compounds derived from gallic acid.
Figure 8:
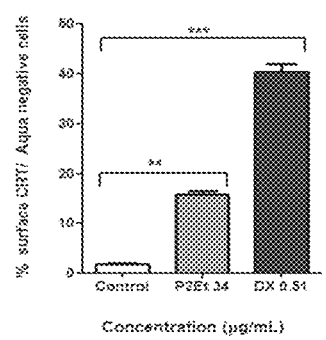
Figure 8:
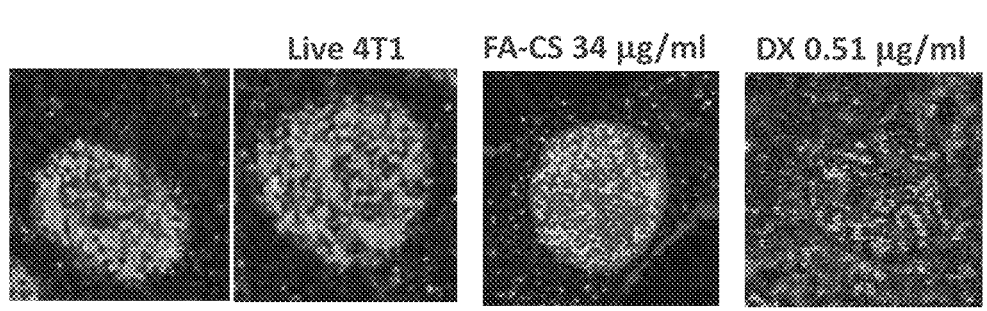

FIG. 8 shows that the treatment with the FA-CS combination promotes increased expression of CRT in the membrane of the 4T1 tumor cells. Similarly, this treatment promotes translocation of the HMGB1 protein from the nucleus to the cytoplasm after the treatment. From these results, it may be concluded that treatment with FA-CS induces immunogenic-type death of the tumor cells.

Example 7. Vaccination of BALB/c Mice with 4T1 Cells Pretreated with the FA-CS Combination Promotes the Generation of T CD4+ Lymphocytes Producing IL-2, TNF-α and IFN-γ Ex Vivo To evaluate the effect of vaccination of BALB/c mice with 4T1 tumor cells pretreated in vitro with the FA-CS combination on the induction of an immune response, 4T1 cells were treated with the negative control (ethanol), the FA-CS combination (34 μg/ml), or doxorubicin (0.51 ug/ml) for 48 hours. After the treatment, the cells were injected into the footpad of BALB/c mice. 7 days later, the popliteal lymph nodes (PLN) were obtained and cultured ($1 \times 10^6$) for 1 hour in the presence or absence of phorbol myristate acetate (PMA)/Ionomycin (Becton Dickinson), followed by addition of brefeldin A (6 hours at 37° C.). These cells were marked with a viability dye (LIVE/DEAD Aqua fluorescent reactive dye, Molecular Probes) for 20 minutes at room temperature (RT) and with monoclonal antibodies specific for: Rat anti-mouse CD3-Alexa Fluor 647 (clone 17A2), Rat anti-mouse CD4-PerCP (clone RM4-5), Rat anti-mouse CD8-PE (clone 53-6.7) (Becton Dickinson) for 30 minutes at 4° C. Next, the cells were fixed and permeabilized using the BD Cytofix/Cytoperm Plus kit (Becton Dickinson) and labeled intracellularly with: Rat anti-mouse IL-2-FITC, Rat anti-mouse TNF-PE Cy7 (clone MP6-XT22) and Rat anti-mouse IFN-γ-Alexa Fluor 700 (clone XMG1.2) (Becton Dickinson) for 30 minutes at 4° C. The cells were taken up on an FACSAria II flow cytometer and analyzed with the FlowJo software.

Figure 9:
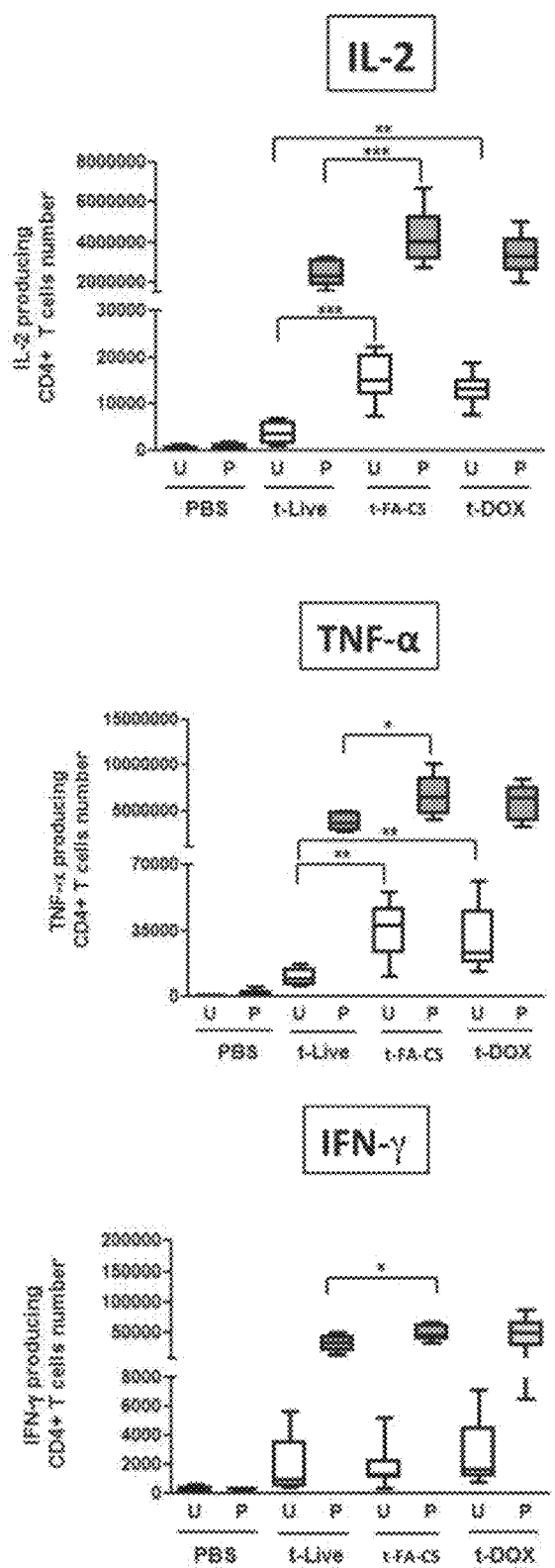
FIG. 9 shows how vaccination with tumor cells treated with the combination of FA-CS and DOX promotes the generation of LT CD4+ producing cytokines IL-2, IFN-γ and TNF-α.

It may be seen in FIG. 9 that the mice that were vaccinated with the 4T1 tumor cells pretreated in vitro with the FA-CS combination (t-FA-CS) generate a larger number of T CD4+ lymphocytes producing IL-2, TNF-α and IFN-γ in comparison with the mice vaccinated with live 4T1 cells (t-LIVE).

Example 8. Vaccination of BALB/c Mice with 4T1 Cells Pretreated with the FA-CS Combination Promotes the Production of IL-4 and IL-5 in Response to the Antigenic Stimulus To evaluate the effect of vaccination with 4T1 cells pretreated in vitro in BALB/c mice, 4T1 cells were treated with the negative control (ethanol), the FA-CS combination (34 µg/ml) or doxorubicin (0.51 µg/ml) for 48 hours. After the treatment, the cells were injected into the footpad of BALB/c mice. 7 days later, the popliteal lymph nodes (PLN) were obtained and cultured ($1 \times 10^6$) for 72 hours in RPMI 1640 medium supplemented with 50 mM of 2-mercaptoethanol in the presence of 0.5 µg/ml of anti-mouse CD28 (clone 37.51, Becton Dickinson) and 1 µg/ml of anti-mouse CD49d (Clone R1-2, Becton Dickinson). In a few wells, re-stimulation was performed with a lysate of 4T1 cells (100 µg) or with the same volume of PBS. After the 72 hours, the supernatants were collected and stored at −70° C. until the time of processing. The production of cytokines in the culture supernatant was evaluated using the Becton Dickinson cytometric bead array (CBA) kit for mouse inflammatory cytokines (Becton Dickinson). The evaluated cytokines were IL-4, IL-5, TNF-α or IFN-γ. The cytokines were taken up using an FACSAria II and analyzed using the FCAP Array program (Becton Dickinson). The treatments were performed in triplicate and the results expressed as the mean of the ranges of 3 independent experiments.

Figure 10:
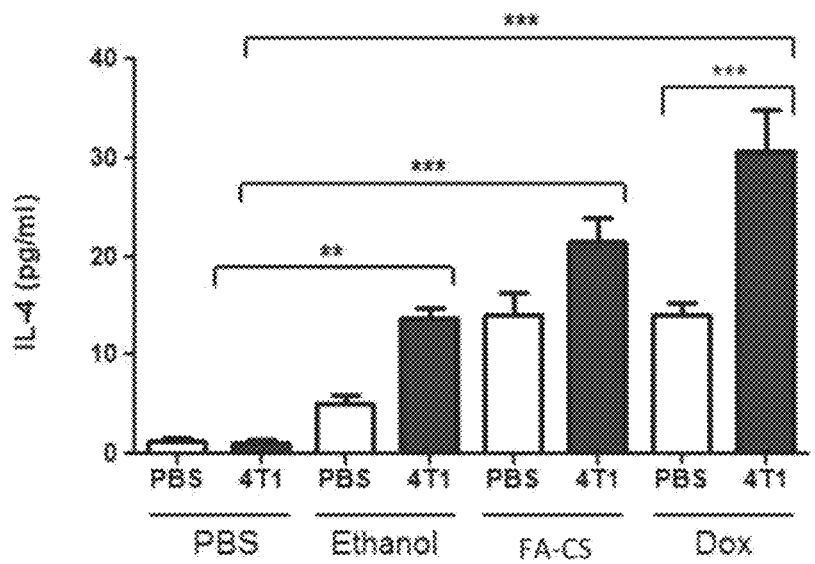
FIG. 10 shows the production of intrinsic cytokines of memory cells in response to the antigen, obtained from the popliteal ganglion of mice vaccinated with tumor cells treated with a combination of the invention or with doxorubicin.
Figure 10:
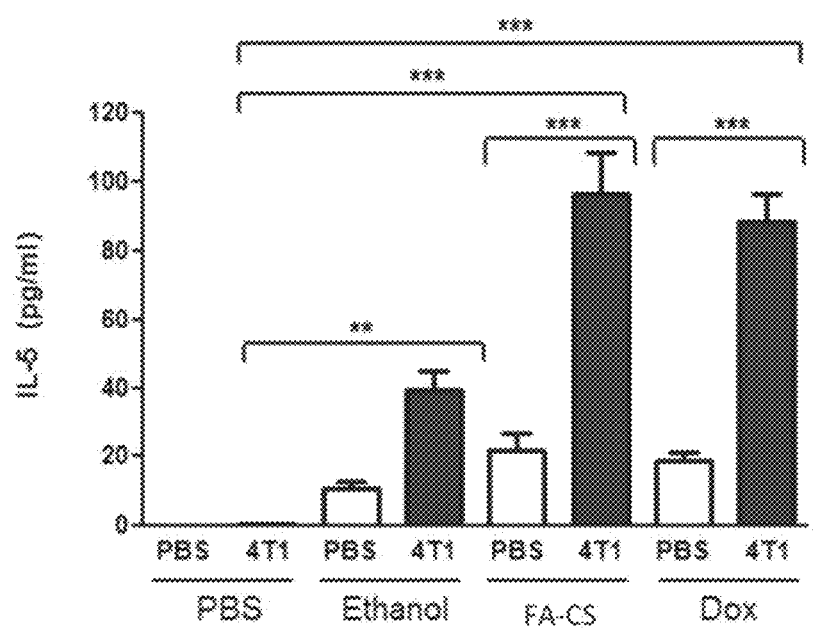

In FIG. 10, it may be seen that the vaccination of BALB/c mice with t-FA-CS promotes the production of IL-4 and IL-5. This increase is more clearly evident when the cells were cultured in the presence of a lysate of 4T1 cells, suggesting that the production of these cytokines is antigen-dependent.

REFERENCES

Chai, S., K. K. To, et al. (2010). "Circumvention of multidrug resistance of cancer cells by Chinese herbal medicines." *Chin Med* 5: 26.

Dewan, M. Z., H. Terunuma, et al. (2005). "Natural killer cells in breast cancer cell growth and metastasis in SCID mice." *Biomed Pharmacother* 59 Suppl 2: S375-379.

Fiuza, S. M., C. Gomes, et al. (2004). "Phenolic acid derivatives with potential anticancer properties—a structure-activity relationship study. Part 1: methyl, propyl and octyl esters of caffeic and gallic acids." *Bioorg Med Chem* 12(13): 3581-3589.

Fulton, A., F. Miller, et al. (2006). "Prospects of controlling breast cancer metastasis by immune intervention." *Breast Dis* 26: 115-127.

Gali, H. U., E. M. Perchellet, et al. (1992). "Hydrolyzable tannins: potent inhibitors of hydroperoxide production and tumor promotion in mouse skin treated with 12-O-tetradecanoylphorbol-13-acetate in vivo." *Int J Cancer* 51(3): 425-432.

Gandhi, N. M. and C. K. Nair (2005). "Protection of DNA and membrane from gamma radiation induced damage by gallic acid." *Mol Cell Biochem* 278(1-2): 111-117.

Gensler, H. L., K. E. Gerrish, et al. (1994). "Prevention of photocarcinogenesis and UV-induced immunosuppression in mice by topical tannic acid." *Nutr Cancer* 22(2): 121-130.

Locatelli, C., R. Rosso, et al. (2008). "Ester derivatives of gallic acid with potential toxicity toward L1210 leukemia cells." *Bioorg Med Chem* 16(7): 3791-3799.

Mansfield, A. S., P. Heikkila, et al. (2011). "Metastasis to sentinel lymph nodes in breast cancer is associated with maturation arrest of dendritic cells and poor co-localization of dendritic cells and CD8+T cells." *Virchows Arch* 459(4): 391-398.

Morrison, B. J., C. W. Schmidt, et al. (2008). "Breast cancer stem cells: implications for therapy of breast cancer." *Breast Cancer Res* 10(4): 210.

Mukhtar, H., M. Das, et al. (1988). "Exceptional activity of tannic acid among naturally occurring plant phenols in protecting against 7,12-dimethylbenz(a)anthracene-, benzo(a)pyrene-, 3-methylcholanthrene-, and N-methyl-N-nitrosourea-induced skin tumorigenesis in mice." *Cancer Res* 48(9): 2361-2365.

Richardson, M. A. (2001). "Biopharmacologic and herbal therapies for cancer: research update from NCCAM." *J Nutr* 131(11 Suppl): 3037S-3040S.

Serrano, A., C. Palacios, et al. (1998). "Derivatives of gallic acid induce apoptosis in tumoral cell lines and inhibit lymphocyte proliferation." *Arch Biochem Biophys* 350(1): 49-54.

Visonneau, S., A. Cesano, et al. (1998). "Growth characteristics and metastatic properties of human breast cancer xenografts in immunodeficient mice." *Am J Pathol* 152 (5): 1299-1311.

Williams, S. S., T. R. Alosco, et al. (1993). "The study of human neoplastic disease in severe combined immunodeficient mice." *Lab Anim Sci* 43(2): 139-146.

The invention claimed is:

1. A combination comprising:
    (a) between 75% and 85% by weight, relative to the total weight of the combination, of one or more compounds selected from the group consisting of:
    3,4,5-trihydroxy-1-(3,4,5-trihydroxybenzoyl)oxycyclohexane-1-carboxylic acid (1-O-galloylquinic acid),
    1,4,5-trihydroxy-3-(3,4,5-trihydroxybenzoyl)oxycyclohexane-1-carboxylic acid (3-O-galloylquinic acid),
    1,3,5-trihydroxy-4-(3,4,5-trihydroxybenzoyl)oxycyclohexane-1-carboxylic acid (4-O-galloylquinic acid),
    1,3,4-trihydroxy-5-(3,4,5-trihydroxybenzoyl)oxycyclohexane-1-carboxylic acid (5-O-galloylquinic acid),
    1,4-dihydroxy-3,5-bis[(3,4,5-trihydroxybenzoyl)oxy]cyclohexane-1-carboxylic acid (3,5-O-digalloylquinic acid),
    1,5-dihydroxy-3,4-bis[(3,4,5-trihydroxybenzoyl)oxy]cyclohexane-1-carboxylic acid (3,4-O-digalloylquinic acid),
    1,3-dihydroxy-4,5-bis[(3,4,5-trihydroxybenzoyl)oxy]cyclohexane-1-carboxylic acid (4,5-O-digalloylquinic acid),
    4-hydroxy-1,3,5-tris[(3,4,5-trihydroxybenzoyl)oxy]cyclohexane-1-carboxylic acid (1,3,5-tri-O-galloylquinic acid),
    5-hydroxy-1,3,4-tris[(3,4,5-trihydroxybenzoyl)oxy]cyclohexane-1-carboxylic acid (1,3,4-tri-O-galloylquinic acid),
    3-hydroxy-1,4,5-tris[(3,4,5-trihydroxybenzoyl)oxy]cyclohexane-1-carboxylic acid (1,4,5-tri-O-galloylquinic acid), and
    1-hydroxy-3,4,5-tris[(3,4,5-trihydroxybenzoyl)oxy]cyclohexane-1-carboxylic acid (3,4,5-tri-O-galloylquinic acid);
    (b) between 10% and 20% by weight, relative to the total weight of the combination, of one or more compounds selected from the group consisting of:
    3,4-dihydroxy-5-(3,4,5-trihydroxybenzoyl)oxybenzoate, methyl 3,4-dihydroxy-5-(3,4,5-trihydroxybenzoyl)oxybenzoate, and methyl 3,4,5-trihydroxybenzoate;

(c) between 0.1% and 8% by weight, relative to the total weight of the combination, of the compound:

3,4,5,6-tetrakis[(3,4,5-trihydroxybenzoyl)oxy]oxan-2-yl] methyl 3,4,5-trihydroxybenzoate (pentagalloyl glucose);

and (d) an effective amount of other topoisomerase inhibitors or mitosis inhibitors, wherein the combination provides for synergistic effect in the treatment of cancer.

2. A pharmaceutical combination comprising:

(a) between 75% and 85% by weight, relative to the total weight of the combination, of one or more compounds selected from the group consisting of:

3,4,5-trihydroxy-1-(3,4,5-trihydroxybenzoyl)oxycyclohexane-1-carboxylic acid (1-O-galloylquinic acid), 1,4,5-trihydroxy-3-(3,4,5-trihydroxybenzoyl)oxycyclohexane-1-carboxylic acid (3-O-galloylquinic acid), 1,3,5-trihydroxy-4-(3,4,5-trihydroxybenzoyl)oxycyclohexane-1-carboxylic acid (4-O-galloylquinic acid), 1,3,4-trihydroxy-5-(3,4,5-trihydroxybenzoyl)oxycyclohexane-1-carboxylic acid (5-O-galloylquinic acid), 1,4-dihydroxy-3,5-bis[(3,4,5-trihydroxybenzoyl)oxy]cyclohexane-1-carboxylic acid (3,5-O-digalloylquinic acid), 1,5-dihydroxy-3,4-bis[(3,4,5-trihydroxybenzoyl)oxy]cyclohexane-1-carboxylic acid (3,4-O-digalloylquinic acid), 1,3-dihydroxy-4,5-bis[(3,4,5-trihydroxybenzoyl)oxy]cyclohexane-1-carboxylic acid (4,5-O-digalloylquinic acid), 4-hydroxy-1,3,5-tris[(3,4,5-trihydroxybenzoyl)oxy]cyclohexane-1-carboxylic acid (1,3,5-tri-O-galloylquinic acid), 5-hydroxy-1,3,4-tris[(3,4,5-trihydroxybenzoyl)oxy]cyclohexane-1-carboxylic acid (1,3,4-tri-O-galloylquinic acid), 3-hydroxy-1,4,5-tris[(3,4,5-trihydroxybenzoyl)oxy]cyclohexane-1-carboxylic acid (1,4,5-tri-O-galloylquinic acid), and 1-hydroxy-3,4,5-tris[(3,4,5-trihydroxybenzoyl)oxy]cyclohexane-1-carboxylic acid (3,4,5-tri-O-galloylquinic acid);

(b) between 10% and 20% by weight, relative to the total weight of the combination, of one or more compounds selected from the group consisting of:

3,4-dihydroxy-5-(3,4,5-trihydroxybenzoyl)oxybenzoate, methyl 3,4-di hydroxy-5-(3,4,5-trihydroxybenzoyl)oxybenzoate, and methyl 3,4,5-trihydroxybenzoate, (c) between 0.1% and 8% by weight, relative to the total weight of the combination, of the compound:

3,4,5,6-tetrakis[(3,4,5-trihydroxybenzoyl)oxy]oxan-2-yl] methyl 3,4,5-trihydroxybenzoate (pentagalloyl glucose);

(d) an effective amount of other topoisomerase inhibitors or mitosis inhibitors;

and (e) one or more pharmaceutically acceptable excipients for the adaptation of a liquid, solid or heterodispersed pharmaceutical form, wherein the pharmaceutical combination provides for synergistic effect in the treatment of cancer.

3. The combination according to claim 1, wherein in (a): one or more compounds selected from the group consisting of 3,4,5-trihydroxy-1-(3,4,5-trihydroxybenzoyl) oxycyclohexane-1-carboxylic acid (1-O-galloylquinic acid), 1,4,5-trihydroxy-3-(3,4,5-trihydroxybenzoyl) oxycyclohexane-1-carboxylic acid (3-O-galloylquinic acid), 1,3,5-trihydroxy-4-(3,4,5-trihydroxybenzoyl) oxycyclohexane-1-carboxylic acid (4-O-galloylquinic acid), and 1,3,4-trihydroxy-5-(3,4,5-trihydroxybenzoyl)oxycyclohexane-1-carboxylic acid (5-0-galloylquinic acid) are present in a range of 55-70 w/w % of the compounds in (a);

one or more compounds selected from the group consisting of 1,4-dihydroxy-3,5-bis[(3,4,5-trihydroxybenzoyl)oxy]cyclohexane-1-carboxylic acid (3,5-O-digalloylquinic acid), 1,5-dihydroxy-3,4-bis[(3,4,5-trihydroxybenzoyl)oxy]cyclohexane-1-carboxylic acid (3,4-O-digalloylquinic acid), and 1,3-dihydroxy-4,5-bis[(3,4,5-trihydroxybenzoyl)oxy]cyclohexane-1-carboxylic acid (4,5-O-digalloylquinic acid) are present in a range of 10-20 w/w % of the compounds in (a); and one or more compounds selected from the group consisting of 4-hydroxy-1,3,5-tris[(3,4,5-trihydroxybenzoyl) oxy]cyclohexane-1-carboxylic acid (1,3,5-tri-O-galloylquinic acid), 5-hydroxy-1,3,4-tris[(3,4,5-trihydroxybenzoyl)oxy]cyclohexane-1-carboxylic acid (1,3,4-tri-O-galloylquinic acid), 3-hydroxy-1,4,5-tris [(3,4,5-trihydroxybenzoyl)oxy]cyclohexane-1-carboxylic acid (1,4,5-tri-O-galloylquinic acid), and 1-hydroxy-3,4,5-tris[(3,4,5-trihydroxybenzoyl)oxy] cyclohexane-1-carboxylic acid (3,4,5-tri-O-galloylquinic acid) are present in a range of 1-10 w/w % of the compounds in (a).

4. The combination according to claim 1, wherein in (b): one or more compounds selected from the group consisting of 3,4-dihydroxy-5-(3,4,5-trihydroxybenzoyl)oxybenzoate and methyl 3,4-dihydroxy-5-(3,4,5-trihydroxybenzoyl)oxybenzoate are present in a range of 1-10 w/w % of the compounds in (b); and methyl 3,4,5-trihydroxybenzoate is present in a range of 0.1-5 w/w % of the compounds in (b).

5. The pharmaceutical combination according to claim 2, wherein in (a):

one or more compounds selected from the group consisting of:

3,4,5-trihydroxy-1-(3,4,5-trihydroxybenzoyl)oxycyclohexane-1-carboxylic acid (1-O-galloylquinic acid), 1,4, 5-trihydroxy-3-(3,4,5-trihydroxybenzoyl)oxycyclohexane-1-carboxylic acid (3-O-galloylquinic acid), 1,3, 5-trihydroxy-4-(3,4,5-trihydroxybenzoyl) oxycyclohexane-1-carboxylic acid (4-O-galloylquinic acid), and 1,3,4-trihydroxy-5-(3,4,5-trihydroxybenzoyl)oxycyclohexane-1-carboxylic acid (5-O-galloylquinic acid) are present in a range of 55-70 w/w % the compounds in (a);

one or more compounds selected from the group consisting of 1,4-dihydroxy-3,5-bis[(3,4,5-trihydroxybenzoyl)oxy]cyclohexane-1-carboxylic acid (3,5-O-digalloylquinic acid), 1,5-dihydroxy-3,4-bis[(3,4,5-trihydroxybenzoyl)oxy]cyclohexane-1-carboxylic acid (3,4-O-digalloylquinic acid), and 1,3-dihydroxy-4,5-bis[(3,4,5-trihydroxybenzoyl)oxy]cyclohexane-1-carboxylic acid (4,5-O-digalloylquinic acid) are present in a range of 10-20 w/w % of the compounds in (a); and one or more compounds selected from the group consisting of 4-hydroxy-1,3,5-tris[(3,4,5-trihydroxybenzoyl) oxy]cyclohexane-1-carboxylic acid (1,3,5-tri-O-galloylquinic acid), 5-hydroxy-1,3,4-tris[(3,4,5-trihydroxybenzoyl)oxy]cyclohexane-1-carboxylic acid (1,3,4-tri-O-galloylquinic acid), 3-hydroxy-1,4,5-tris

[(3,4,5-trihydroxybenzoyl)oxy]cyclohexane-1-carboxylic acid (1,4,5-tri-O-galloylquinic acid), and 1-hydroxy-3,4,5-tris[(3,4,5-trihydroxybenzoyl)oxy]cyclohexane-1-carboxylic acid (3,4,5-tri-O-galloylquinic acid) are present in a range of 1-10 w/w % of the compounds in (a); and wherein in (b):

the one or more compounds selected from the group consisting of 3,4-dihydroxy-5-(3,4,5-trihydroxybenzoyl)oxybenzoate and methyl 3,4-dihydroxy-5-(3,4,5-trihydroxybenzoyl)oxybenzoate are present in a range of 1-10 w/w % of the compounds in (b); and methyl 3,4,5-trihydroxybenzoate is present in a range of 0.1-5 w/w % of the compounds in (b).

6. A method for treating cancer comprising administering one or more doses of the combination of claim 1 to a mammal suffering from cancer.

7. The method of claim 6, further comprising concomitantly or separately administering other chemotherapeutic agents selected from the group consisting of alkylating agents and antimetabolites, wherein the combination of (a), (b), and (c) components of claim 1 reduces effective doses of single chemotherapy with component (d) or the other chemotherapeutic agents.

8. The method of claim 7, wherein the treatment controls primary cancer and/or metastases.

9. The combination according to claim 1, wherein the other topoisomerase inhibitors or mitosis inhibitors are selected from the group consisting of doxorubicin, camptothecin, vincristine and paclitaxel.

10. The pharmaceutical combination according to claim 2, wherein the other topoisomerase inhibitors or mitosis inhibitors are selected from the group consisting of doxorubicin, camptothecin, vincristine and paclitaxel.

11. A coadjuvant of therapy for the treatment of cancer, the coadjuvant comprising the combination of claim 1 wherein the combination of (a), (b), and (c) components reduces effective doses of single chemotherapy with other chemotherapeutic agents selected from the group consisting of topoisomerase inhibitors, mitosis inhibitors, alkylating agents and antimetabolites.

12. A method for treating cancer comprising administering one or more doses of the pharmaceutical combination of claim 2 to a mammal suffering from cancer.

13. The method of claim 12, further comprising concomitantly or separately administering other chemotherapeutic agents selected from the group consisting of alkylating agents and antimetabolites, wherein the combination of (a), (b), and (c) components of claim 2 reduces effective doses of single chemotherapy with component (d) or the other chemotherapeutic agents.

* * * * *